(12) United States Patent
Simonson et al.

(10) Patent No.: US 10,137,000 B1
(45) Date of Patent: Nov. 27, 2018

(54) METHOD AND APPARATUS FOR PLACEMENT INTO IATROGENICALLY CREATED SKELETAL VOIDS

(71) Applicants: Robert E Simonson, Boca Raton, FL (US); David P. Sachs, Boca Raton, FL (US)

(72) Inventors: Robert E Simonson, Boca Raton, FL (US); David P. Sachs, Boca Raton, FL (US)

( * ) Notice: Subject to any disclaimer, the term of this patent is extended or adjusted under 35 U.S.C. 154(b) by 0 days.

(21) Appl. No.: 14/134,379

(22) Filed: Dec. 19, 2013

Related U.S. Application Data

(63) Continuation of application No. 12/315,763, filed on Dec. 5, 2008, now abandoned.

(51) Int. Cl.
*A61F 2/44* (2006.01)

(52) U.S. Cl.
CPC ..................... *A61F 2/44* (2013.01)

(58) Field of Classification Search
CPC . A61F 2/442; A61F 2/4611; A61F 2220/0025
USPC ................... 623/17.11, 17.1, 17.16
See application file for complete search history.

(56) References Cited

U.S. PATENT DOCUMENTS

| | | | |
|---|---|---|---|
| 4,341,206 A | 7/1982 | Perrett et al. | |
| 5,015,247 A | 5/1991 | Michelson | |
| 5,180,382 A | 1/1993 | Frigg et al. | |
| 5,246,458 A | 9/1993 | Graham | |
| 5,324,290 A | 6/1994 | Zdeblick | |
| 5,364,399 A | 11/1994 | Lowery et al. | |
| 5,549,612 A | 8/1996 | Yapp | |
| 6,248,110 B1 * | 6/2001 | Reiley | A61B 10/025 606/192 |
| 6,419,705 B1 * | 7/2002 | Erickson | A61F 2/4455 623/17.11 |
| 6,436,102 B1 | 8/2002 | Ralph et al. | |
| 6,679,886 B2 | 1/2004 | Weikel et al. | |
| 7,094,239 B1 | 8/2006 | Michelson | |
| 7,128,760 B2 | 10/2006 | Michelson | |
| 7,160,304 B2 | 1/2007 | Michelson | |
| 7,226,481 B2 * | 6/2007 | Kuslich | A61B 17/68 623/17.11 |
| 2001/0056302 A1 | 12/2001 | Boyer et al. | |
| 2003/0004575 A1 | 1/2003 | Erickson | |
| 2003/0065396 A1 | 4/2003 | Michelson | |
| 2003/0125747 A1 | 7/2003 | Sproul | |
| 2003/0181982 A1 * | 9/2003 | Kuslich | A61B 17/7055 623/17.16 |

(Continued)

OTHER PUBLICATIONS

Choi et al., "Modified transcoropreal anterior cervical microforaminotomy for cervical radiculopathy: A technical note and early results", Eur Spine J (2007) 16(9): 1387-1393.

*Primary Examiner* — David Isabella
*Assistant Examiner* — Christine Nelson
(74) *Attorney, Agent, or Firm* — Burr & Forman LLP; Jeffrey H. Kamenetsky

(57) ABSTRACT

This invention relates to an implant having the capability of being adjusted to fit symmetrical and asymmetrical shaped voids formed in the bone or outside the bone of a patient. The implant can be individualized so as to accommodate various distortion in the void and can be disposed as a series of similar shaped implants that have different dimensions and/or characteristics to allow the surgeon to select an appropriate implant from said series.

30 Claims, 8 Drawing Sheets

(56) References Cited

U.S. PATENT DOCUMENTS

2003/0195518 A1    10/2003   Cragg
2004/0126407 A1    7/2004   Falahee
2006/0111714 A1    5/2006   Foley
2009/0076555 A1    3/2009   Lowry et al.

\* cited by examiner

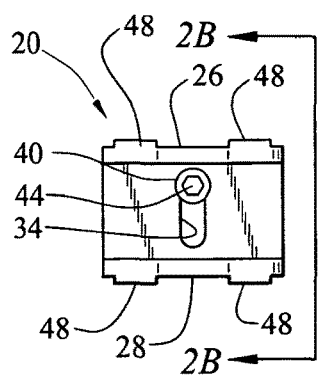
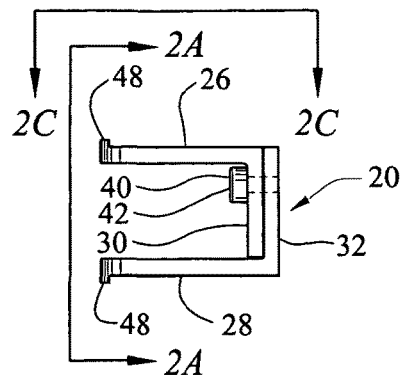
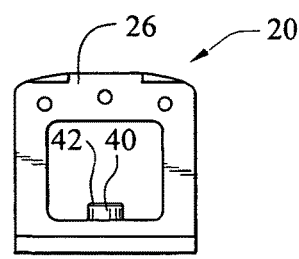
FIG. 2A  FIG. 2B  FIG. 2C
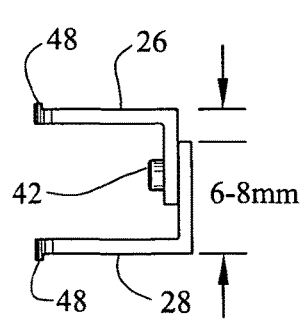
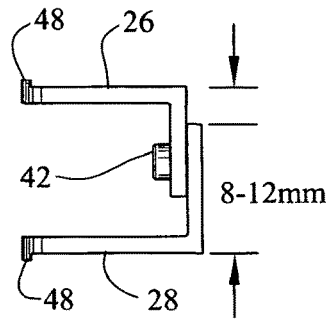
FIG. 3A  FIG. 3B
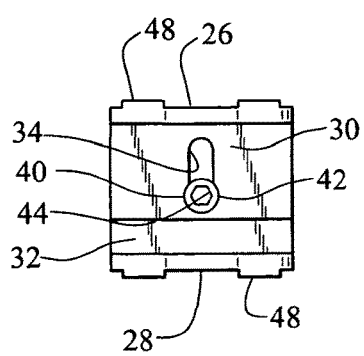
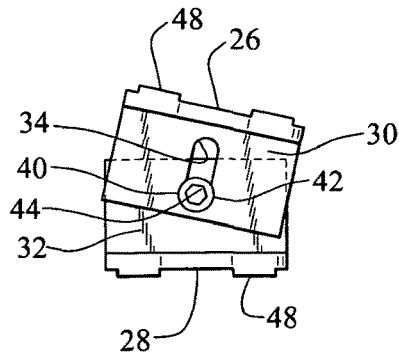
FIG. 4A  FIG. 4B

METHOD AND APPARATUS FOR PLACEMENT INTO IATROGENICALLY CREATED SKELETAL VOIDS

CROSS REFERENCE TO RELATED APPLICATIONS

This continuation application claims priority to U.S. application Ser. No. 12/315,763, entitled "Method and Apparatus For Placement into Iatrogenically Created Skeletal Voids", filed Dec. 5, 2008, the entirety of which is incorporated herein by reference.

RELATED APPLICATIONS

The surgical method disclosed in U.S. patent application Ser. No. 12/069,654 filed on Feb. 12, 2008 describes an intravertebral corpectomy medical procedure that serves to remove bone for defining space to allow the surgeon to perform a surgical procedure to remove a pathology at a specific target in the body of a patient. This patent application was filed by the same inventors as this related patent application and is incorporated by reference in its entirety into this application. This intravertabral corpectomy requires an implant and the invention disclosed in the present application is particularly efficacious for this procedure.

FEDERALLY SPONSORED RESEARCH OR DEVELOPMENT

Not applicable

TECHNICAL FIELD

This invention relates to the method and apparatus for repairing iatrogenically created skeletal voids that may take the form of being regularly or irregularly shaped which are created during the performance of a surgical procedure directed to, within, and sometimes through skeletal structures.

BACKGROUND OF THE INVENTION

As is taught in the patent application noted above, it is becoming increasingly important to create temporary voids in bone or in spaces between bones, as for example, by the removal of the disc in the spine. In certain surgical procedures the operation creates a void that is wholly within the bone, and in other surgical procedures the void is completely through the bone and the depth of the void is predicated on the particular pathology being treated. When the medical procedure has been performed upon or through the bone, the surgically created void must be repaired to assure a successful surgical outcome and improve the healing process. The current state of repairing such voids is made up of three distinct categories; moldable fillers or flowable materials such as pastes, putties and cements; fixed dimension cages of various shapes including boxes, cylinders, and threaded devices which can be screwed into place; and adjustable devices. The final category of devices does allow some modification of the implant to fit the size of the void but only in a primarily symmetrical fashion. In other words, the height can be adjusted higher or lower by manipulating a threaded portion thus jacking it up or down, or other designs allowing for larger or smaller plates to be added to the side creating greater or lesser height. These adjustable devices allow for symmetrical adjustment but do not provide much or any ability to be adjusted asymmetrically to match irregularities in the bony void. Both sides along with the tops and the bottoms of these implants adjust to form a regular shape. Requiring the intraoperative creation of a near perfectly formed regular shape (polygonal) to receive the implant places an undo burden upon the surgeon by adding a difficult carpenter's task to the already complex task of performing the operation.

During a surgical procedure, the size and the shape of the void created in the bone will be dictated by a number of productive factors. These factors include; the patients anatomy, the procedure to be performed, the size, shape and make up of the pathology, the needed exposure for treatment, the size of the instruments needed to pass into or through the void, and among others, the surgeon's preferred technique. The reasons listed above, dictate the nature of the void created to treat the patient and achieve the surgical goals, which will lead to the overall well being of the patient. Those same reasons usually lead to a surgically created void that is not formed quadrilaterally, or cylindrically, or in some other symmetrically shaped configuration. These reasons usually dictate the creation of an irregular shape. Unfortunately, the medical community has not been provided with an adequately acceptable implant that accommodates these irregularly shaped configurations of the void. What is needed is an infinitely adjustable otherwise void-matching form-following implant made from a metallic or other material so as to supplant other filler techniques such as putties or cements, which are often not appropriate to fill a void. Heretofore, in these types of procedures that leave a void, the surgeon is burdened with the unfortunate task of adding complex carpentry to the final step of many orthopedic, neurosurgical, or other specialties' procedures. After the goal of the surgery has been accomplished the surgeon must unproductively modify the size and shape of the skeletal void solely for the purpose of shaping the void to receive an implant of the types that are currently available and which do not provide adequate adjustability. This situation provides an example of the age-old expression; you cannot put a square peg into a round hole. At this stage in a surgical procedure, in order to accommodate the shape of a selected implant it will often be necessary for the surgeon to remove substantial additional healthy tissue to create a void that matches the shape of the implant. In addition to the additional removal of healthy tissue being unproductive to the well being of the patient, it is often extremely difficult and time consuming. The purpose of this invention is to obviate these procedures as will be explained in further detail herein below.

A workshop-based carpenter is often privileged to work with a wide array of tools at his/her disposal. Maybe a large bench with table saws, jigsaws, clamps, glues, fillers, sandpaper and most importantly, plenty of time and space. Similarly, the biomedical implant engineers are usually working and developing their theories and prototypes in a lab on artificial bone models using machining tools such as a mill at a workstation or in otherwise, exacting non challenging environments, which make the creation of a perfect square, rectangle, ovoid, or some other predetermined engineering shape (regular shape) a practical task. A surgeon on the other hand, is almost always in a stressed and or otherwise challenged environment. The surgeon is usually working in a hole, a hole that is constantly oozing blood, working with sharp cutting implements while surrounded by delicate life preserving anatomical structures, limited in scope of movement, and often times with limited visualization among other frequent challenges. A surgeon is under terrific time constraints dictated by the health of the patient, the limitations and dangers of anesthesia, the continual bleeding of the now dissected patient, and more so today than ever before the present issues relating to the high hourly costs associated with running a hospital operating room. Any addition of time adds to and complicates these factors, likewise any reduction in time subtracts from these factors and works in the patient's favor. For the surgeon to spend several minutes to an hour or more performing carpentry tasks upon the iatrogenically created skeletal void solely for the purpose of modifying its form to receive a preformed or inadequately adjustable shape adds to all of the previously stated costs and subtracts from the overall well being of the patient. It is unfortunate, but this is the current state of the art and these events occur everyday in hospitals throughout the country and the world. The accommodation of a regular shape (the implant) by an irregular shape (the iatrogenically created skeletal void) requires the removal of additional skeletal tissue to modify the irregular shape into a regular shape to match the implant. If the shape of the skeletal void does not ultimately and adequately match the implant, the implant will have a poor fit and be at risk of not serving its desired function. This happens from time to time and can result in the implant migrating to an unplanned and undesirable location or other issues, many of which could require additional surgeries to repair the unplanned complication.

In accordance with this invention, we provide an implant that is inserted into the void and is adjustable to universally contact the irregular edges of the patient's bony anatomy. What is contemplated is that after the surgeon has performed a procedure upon or through a bone and created a skeletal void, without significantly altering the size and shape of void, we provide for the surgeon a series of the inventive implants which allows the surgeon to select one of the inventive implants that will most closely fit into the void, and then place the inventive implant selected, into the void and expand it universally to contact the irregular edges of the patient's bony anatomy in its current form. After the step of placing, expanding and tightening the implant into place, the implant can be filled with a biocompatible material according to the preference of the surgeon or the needs of the patient. Depending on the biocompatible material selected, or the preference of the surgeon, the surgeon may decide whether or not to place a cover over the implant. At this point the surgeon may move forward to complete the final steps of the surgery according to traditionally accepted medical procedures.

The object of this invention is to create a successful and repeatable method of surgically creating and repairing an operative pathway into or through bone. Also disclosed is a method for creating and repairing a surgically created void in bone that does not pass beyond the bone itself. It is common for surgeons to remove a bone in its entirety when it obstructs the surgical pathway to a targeted pathologic or anatomic target. This method of removing the entirety of the bone has historically been the standard of care and is commonplace today. This is primarily because there has not been an effective and predictably repeatable method of traversing bone to create a surgical pathway to perform a surgical procedure that also enabled the surgeon to repair and reconstruct the bone through which the surgical pathway was created.

SUMMARY OF THE INVENTION

An object of this invention is to provide a method of repairing surgically created skeletal voids and pathways by placing an asymmetrically (irregular shape) variably expandable non fluid-flowing apparatus able to expand in multiple planes of section, into the skeletal defect to aid in the healing of the bone.

A feature of the implant of this invention is the ability to expand it in a non-uniform asymmetrical manner. The implant may be selected from a series of implants provided to the surgeon. With the implant, initially being in a collapsed state, smaller then the skeletal void to be filled, the skeletal void may primarily remain in a shape and size dictated by the surgeon's preference and technique. Once placed into the skeletal void the implant may be expanded to contact the outer walls of the skeletal void and then secured in its selected form. The void or channel may be in a spinal vertebral body or any other part of the body. Importantly, the expansion of the inventive implant does not need to follow a purely lineal direction. The inventive device has the ability to expand at irregular angles needed to properly interface with the patient's bony anatomy in the irregularly shaped iatrogenically created surgical void.

A feature of the apparatus is the option of an open framework, verses only a solid or mostly solid plate, at its point of contact with bone. This permits the implant to accommodate for bony ingrowths. More clearly, the superior and inferior contact plates do not need to be completely solid but may be only a framework. As most surgeons prefer to pack an implant with a material that promotes bony ingrowths, having a mostly open framework at the points of contact with the patient's bone marrow allows for the patient's bone to grow into and through the implant allowing for a more complete healing process for the patient. Additionally the open framework of the ends of the inventive implant allow for the irregular, sometimes jagged, edges of the irregular iatrogenically created surgical skeletal void to fit into the implant. Instead of the surgeon having to prepare the ends of the void to fit a pre-engineered shape, the irregularities of the patient's bone can fit into the implant. The implant's ability to accommodate the irregularities of the patient's bone void not only saves the surgeon time and frustration, it can aid in the healing of the surgical site.

A feature of this apparatus is the ability to also have a less open framework if the patient's needs indicated such, or a combination hybrid wherein one end of the implant framework is mostly closed and one end of the framework is mostly open.

A feature of the implant is a joint that allows the implant to be expanded, and to be expanded in a multitude of various angles and dimensional variations.

The importance of the above stated features is realized in many different procedures. An example of one, which will utilize many of the features of the inventive device, is the treatment of iatrogenically created intravertebral corpectomy defects. This type of procedure is performed as part of a surgery to the spine. This procedure removes a portion of the interior of a vertebral body as part of the exposure procedure. This intravertebral corpectomy would commonly leave a very irregular shape after the removal of bone. It is advantageous to leave the irregularities of the void as is, thus reducing the amount of bone removed. The advantages of leaving the irregularities include among many, avoiding injury to the endplates and discs above and below the intravertebral corpectomy, maintaining the vertebra in a better structural state when it receives the implant, and requiring less bone healing to make the vertebral body whole, all contributing to a speedier recovery for the patient. This inventive implant will fit into the void and expand at irregular angles if needed to fit the void in its current state allowing the surgery to progress in a timely manner.

The foregoing and other features of the present invention will become more apparent from the following description and accompanying drawings.

BRIEF DESCRIPTION OF THE DRAWINGS

FIG. 2A is a front plan view taken along lines 2A-2A of FIG. 2B illustrating an embodiment of the inventive implant when in the non-deployed position;

FIG. 2B is a side elevation view taken along lines 2B-2B of FIG. 2A of the embodiment depicted in FIG. 2A;

FIG. 2C is an end view taken along the lines 2C-2C of FIG. 2B in elevation of the embodiment depicted in 2A;

FIG. 3A is a view in elevation which depicts the implant of this invention that represents one size in a series intended to be apart of a kit available of different implant sizes available to a surgeon;

FIG. 3B is a view identical to the unit depicted in FIG. 3A illustrating, as an example, another size of the implant that is intended to be a part of the kit;

FIG. 4A is a front plan view of the embodiment depicted in FIG. 2A illustrating the implant being deployed when used in a symmetrical shaped void;

FIG. 4B is a front plan view of the embodiment depicted in FIG. 4A being deployed when used in a asymmetrical shaped void;

DETAILED DESCRIPTION OF THE INVENTION

While, as will be described herein below, this invention is particularly efficacious with respect to the void created in an intravertabral corpectomy procedure, this inventive implant is also efficacious when used in a void that may be outside the bone, as for example between vertebrae. Further, this invention has particular utility when the void is irregularly shaped (sometimes referred to as asymmetrical). It also has utility when the void is regularly shaped (sometimes referred to as symmetrical). What has been found by experimental laboratory use of this invention is that not only did the implant of this invention have exceptional results in filling the void in an intravertabral corpectomy procedure, it had similar results when applied to non-intravertabral corpectomy procedures. Hence, notwithstanding that this invention is being described as a part of an intravertabral corpectomy procedure we have found that this invention has utility in other types of medical procedures.

An inventive aspect to this new implant disclosure is the development of a new way of performing a surgical procedure upon the spinal vertebra. With the ability of the inventive implant to expand in the versatile manner in which it functions, the implant is able to fill a void made into a spinal vertebra in which the vertebral body is dissected in a manner that is largely parallel to the vertebral endplates and leaves the endplates completely or mostly intact.

This will permit a new type of surgery, which has not been possible prior to this disclosure. This surgery will permit a surgeon to cut into and across a vertebra to gain access to the inside or opposite side of the vertebral bone. This dissection of bone is conducted in a direction that is across the vertebral bone from a primarily anterior position and is toward a primarily posterior direction, leaving the endplates sufficiently intact after the dissection for the placement of the inventive implant. This will permit the endplates to perform their function of supporting and interfacing the vertebral body and intervertebral disc, thus preserving the natural spinal motion of the vertebral body. This is in sharp contrast to all other open surgical procedures, which ultimately eliminate the motion of a vertebral body by fusion or eliminate the natural motion by removing an intervertebral disc.

Figure 5A:
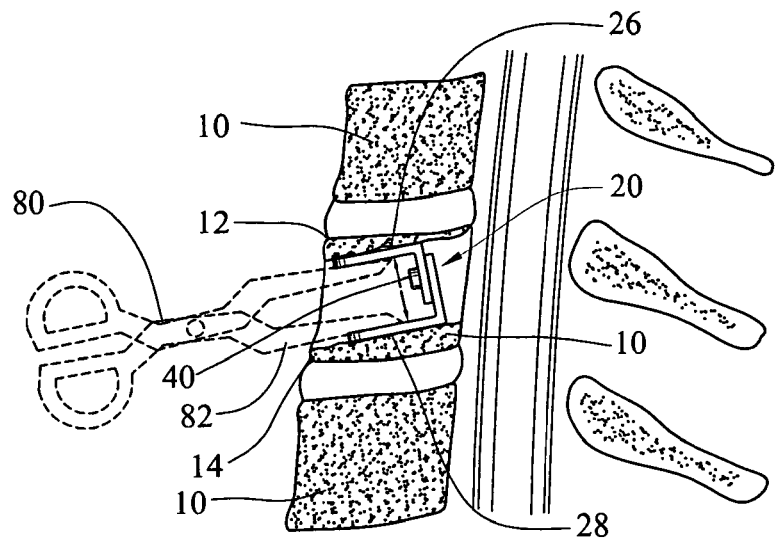
FIG. 5A is a view partly in schematic and partly in phantom illustrating the implant being inserted into the void of a vertebra of the spine of a patient with the use of a forceps-type of tool.

A vertebral body 10 has a superior endplate 12 and an inferior endplate 14 (See FIG. 5A). The ability to operate into and across the vertebral body 10, will allow the surgeon to go through the vertebral bone that is below the superior endplate 12 and above the inferior endplate 14. This will allow the surgeon to operate into or upon targets on the opposite side of a vertebral body while leaving the vertebral endplates sufficiently intact as to allow them to retain their original function.

After a surgical procedure has been performed in the manner as just described, the inventive implant will be able to be placed into the vertebral void and expanded to contact the inside of what remains of the vertebral body and endplates, as will be explained in more detail herein below.

The inventive design of this implant will permit the rebuilding of the vertebral endplates if the vertebral endplates are damaged by disease or by dissection. The superior and inferior aspects of the implant are designed so they may be used as artificial endplates if needed and the implant in its entirety could be used to perform as an artificial vertebral body unlike any previous designs.

Once the implant is in place and sufficiently expanded, the interior of the implant may be filled with a biocompatible fill material that is selected according to the surgeon's preference and the patient's needs. There are many fill materials clinically available for the surgeon to choose from in hospitals across the world.

It is important to note that the inventive implant is to engage interiorly or the interior aspect of the endplates, replacing or supplementing the vertebral corpus and or supplementing the vertebral endplates. This placement will support the intervertebral disc, not replace it, thus avoiding an intervertebral fusion, and maintain the patient's intervertebral joint.

It is important to distinguish this inventive device from previous devices. Previous devices have been made to be placed between joints and in the case of the spine between two or more vertebral bodies. Previous implant designs teach the placement of an implant between two or more vertebral bodies and places the implant in a position to engage the outer most inferior (caudal) surface of superior vertebral body and the outer most superior (cephalad) surface of the inferior vertebral body. This is the opposite of the inventive implant. Hence, as taught in the referenced patent application, the performance of an intravertebral corpectomy avoids the removal of the discs and the surgical procedure is done completely within or through the bone and not between vertebrae.

Figure 1:
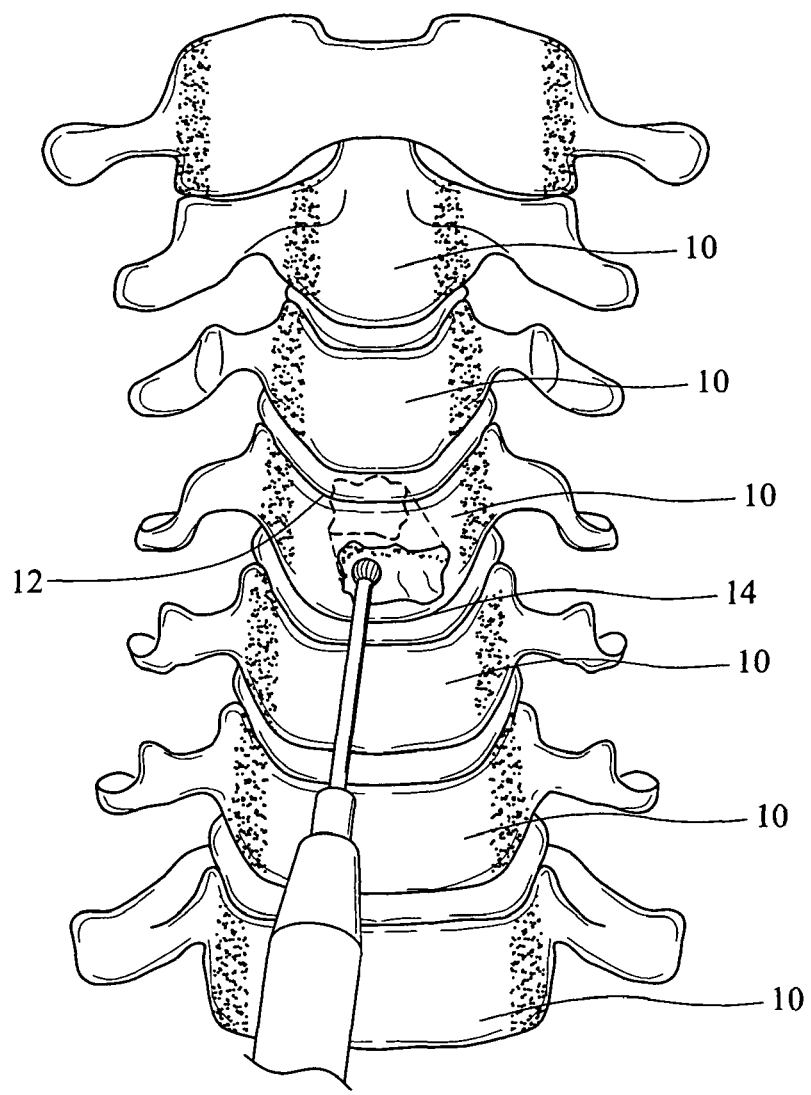
FIG. 1 is a view in schematic illustrating a rendition of a bone being dissected by the surgeon to perform a surgical procedure upon the bone resulting in the creation of an irregularly shaped iatrogenically created surgical void.

The inventive implant is placed against the inner most surfaces of a vertebra, endplate or disc. The superior aspect of the implant will engage the inside surface of superior aspect of the vertebral body, endplate or surface, and the inferior aspect of the implant will engage the inside surface of the inferior aspect of the vertebral body, endplate, or surface. (See FIG. 5A) The next portion of this description will illustrate a series of different implants that are made in accordance with this invention as disclosed in FIGS. 2 through 16. Before referring to the particular implants of this invention, reference should be made to FIG. 1 which is a rendition of a portion of the vertebral column of a human patient and is representative of an anterior view of the cervical vertebrae illustrating one aspect of where this invention is particularly important, although this invention has utility in other bones within the body. As shown in this FIG. 1 the surgeon with the use of a commercially available burring instrument, creates a void in the vertebra which is illustrative of the intravertebral corpectomy. Once the operation is completed the void remains which requires an implant which is the subject of this patent application.

Next, referring to the schematic illustration of FIG. 10, it is shown where the implant of this invention generally illustrated by reference numeral 20 is utilized to be inserted into the bone 22. As described above, once the implant is inserted into the bone, the empty spaces are filled with suitable material. FIGS. 2 through 16 illustrate a number of species of this invention that accommodate different types of voids and are only illustrative of the many variations that this implant can take and are merely representative and are not to be considered as a limitation to the scope of this invention. As seen in the embodiment exemplified in FIGS. 2A, 2B and 2C, the implant generally shown as reference numeral 20 comprises a first L-shaped member 26 and a second complementary L-shaped member 28 where the base arm 30 of member 26 overlies the base arm 32 of member 28 defining together a joint. (all like parts are given like reference numerals notwithstanding the sizes may be different) As best seen in FIG. 12 the overlapping base arm includes a slot 34 and the underlying base arm includes a threaded hole 36 that accepts the complementary threads of the screw 40 (see FIGS. 2A, 2B and 2C) which extends through the slot 34. Screw 40 includes a head 42 with a tool receiving recess 44 that allows the surgeon to thread the screw to tighten and lock the L-shaped members into place. The upper end of the L-shaped members 26 and 28 may include lateral projections 48 that serve to hold the implant in place by either extending into the bone over-lying the top surface of the bone. As is apparent from the foregoing the implant is adjustable both in an axial and an angular direction (see FIGS. 4A and 4B) which is illustrative of filling symmetrical and asymmetrical voids.

As was alluded to in the above paragraph, it is contemplated by this invention to provide to the surgeon a series of different sized implants that will accommodate different sized voids. FIGS. 3A and 3B are illustrative of examples of what a kit of implants can consist of. FIG. 3A represents a small sized implant compared to the FIG. 3B embodiment.

Figure 5B:
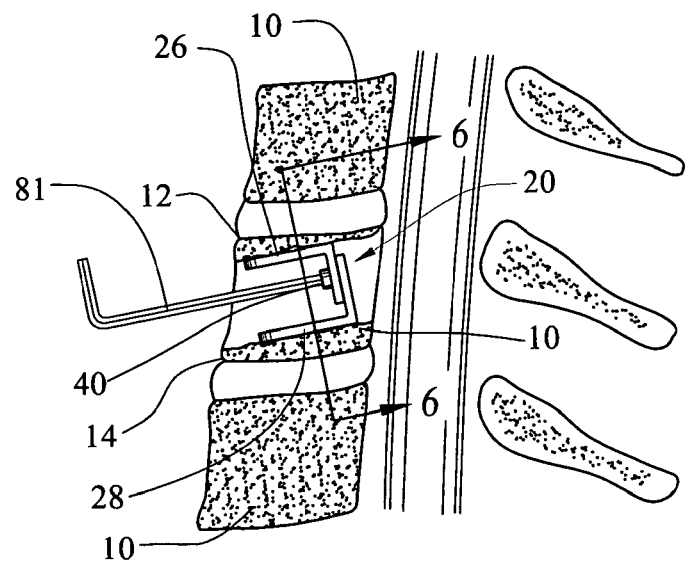
FIG. 5B is a view in schematic illustrating a tool used to tighten the implant of this invention after being inserted into the void of the vertebra as depicted in FIG. 5A.
Figure 6:
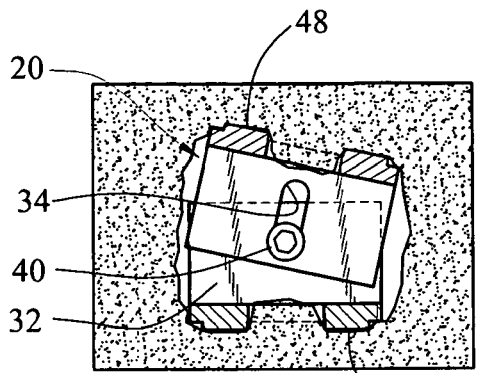
FIG. 6 is a front plan view of the implant of this invention schematically illustrating the implant being deployed in an asymmetrical void.

FIGS. 5A and 5B describe a typical procedure that the surgeon could employ to fit the implant into the void. As shown in FIG. 5A a distracter-like or forceps-like instrument 80 includes the tines 82 that fit internally to the implant 20 such that the surgeon can guide the implant 20 into the desired position within the void. Once this procedure is finished, the surgeon can next, with a proper tool, like a hex head screwdriver 81, tighten the screw to draw the two base arms 30 and 32, respectively, together and lock them in place. It will be appreciated from the foregoing that the surgeon has the capability with the distracter-like instrument to rotate one L-shaped member relative to the other L-shaped member to change the angle to accommodate the type of void illustrated in FIG. 6.

Figure 7:
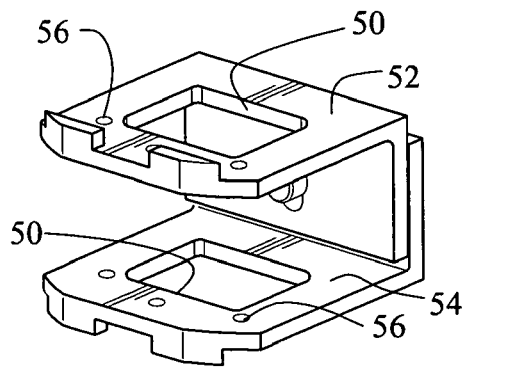
FIG. 7 is a view in perspective illustrating another embodiment of this invention.
Figure 8:
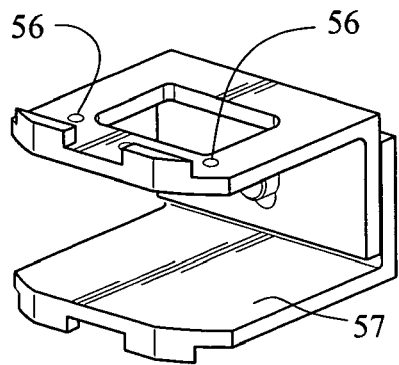
FIG. 8 is a view in perspective illustrating another embodiment of this invention.
Figure 9:
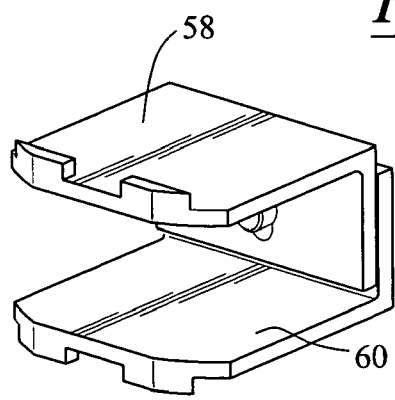
FIG. 9 is a view in perspective illustrating another embodiment of this invention.
Figure 10:
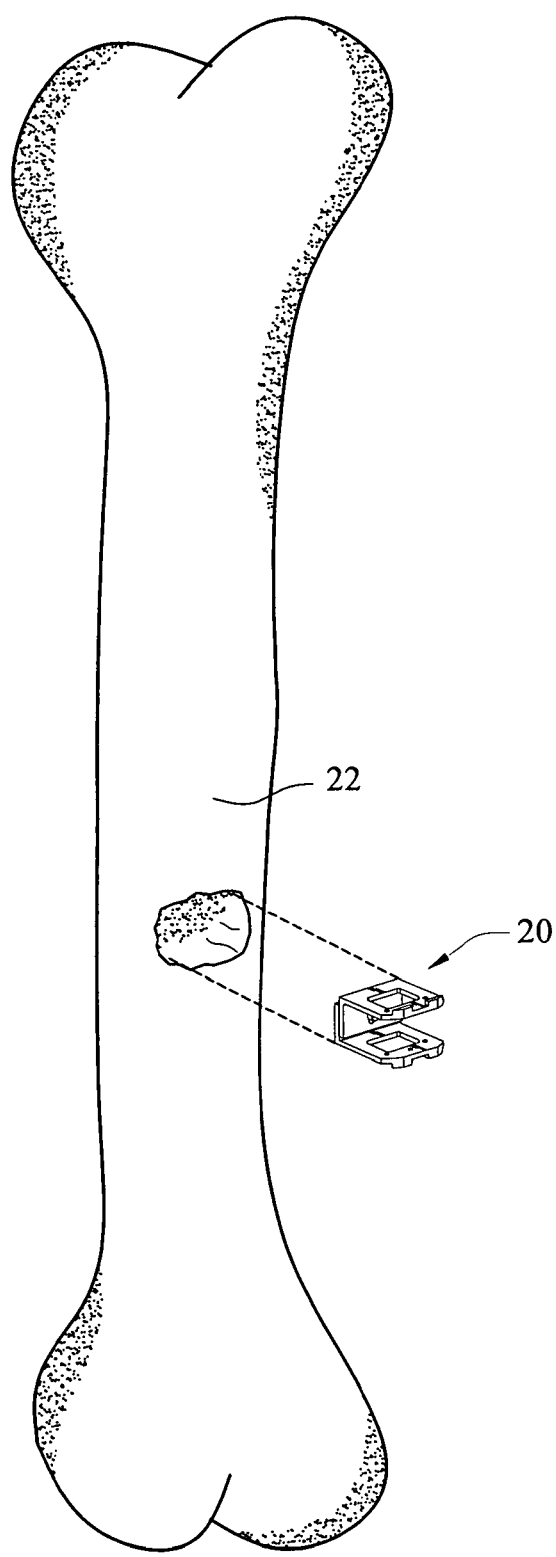
FIG. 10 is a schematic illustration and exploded view showing the implant of this invention in relationship to the void formed in a bone.

FIGS. 7, 8 and 9 exemplify other embodiments of this invention where, as illustrated in FIG. 7, windows 50 are formed in the upstanding arms of the L-shaped members 52 and 54 which serve to define frames which serve to allow the bone tissue to grow around the implant and secure it in place. Holes 56 serve the same purpose. FIGS. 8 and 9 exemplify embodiments where the vertebrae endplate(s) may be removed. As shown in FIG. 8 exemplifies another embodiment of an implant that is designed where one of the L-shaped members 57 is solid, i.e. absent the window, so as to accommodate the situation when one vertebral endplate is removed. And FIG. 9 exemplifies the embodiment of the implant where two vertebrae endplates are removed by including solid arms 58 and 60 of the L-shape members.

Figure 11:
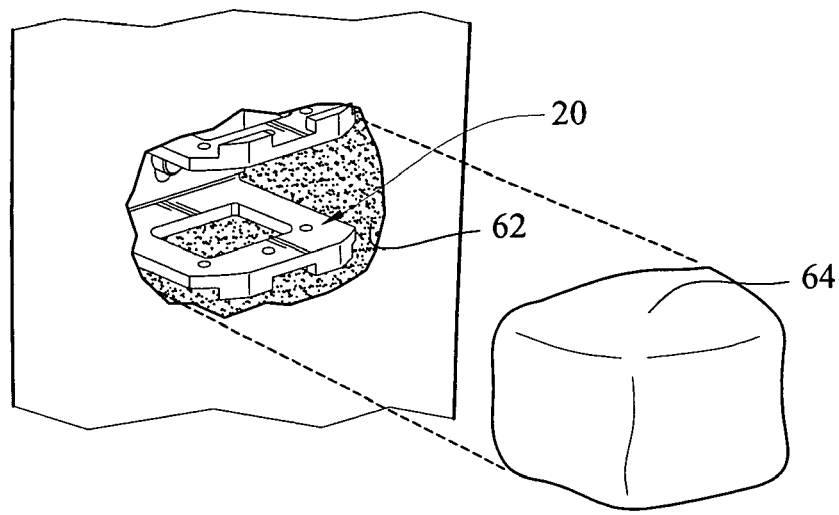
FIG. 11 is a view in schematic illustrating the implant of this invention partially shown in perspective providing a view of the relationship of the bone, void and implant.
Figure 12:
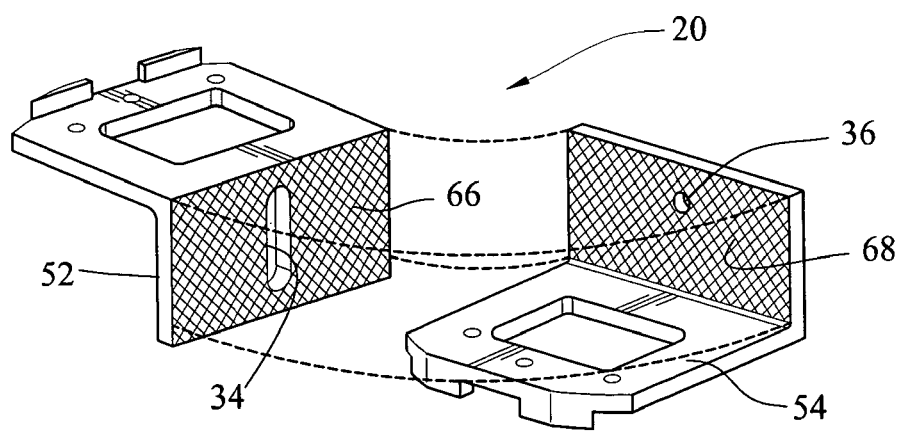
FIG. 12 is an exploded view in perspective illustrating another embodiment of this invention.

FIG. 11 is a schematic view in perspective and a fragmentary view of the implant inserted into the void for illustrating the concept of filling a void 62 with the implant and showing the dimension of the void 62 by depicting what a portion of the removed bone 64 would look like if it were removed in whole.

FIG. 12 is an exploded view in perspective that exemplifies another embodiment of this invention where the mating surfaces 66 and 68 of the L-shaped members 52 and 54, respectively, are roughened, as by knurling or the like.

Figure 13:
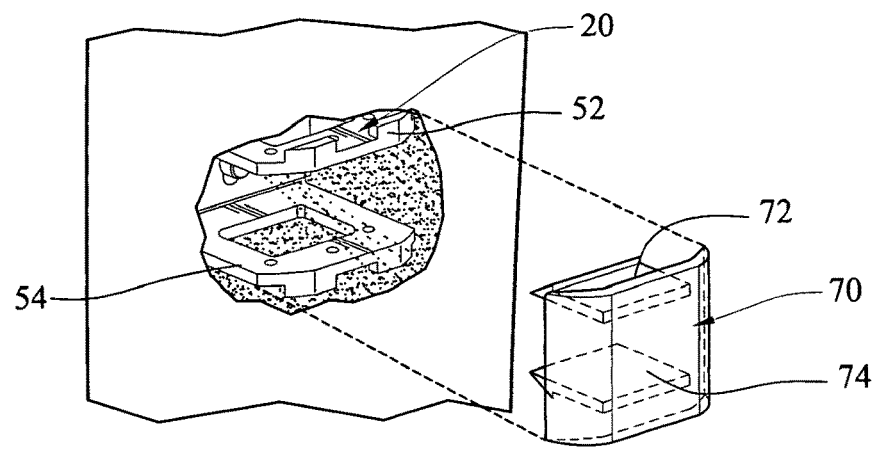
FIG. 13 is a partial view in schematic illustrating a fragmentary view in perspective of the implant of this invention into a void formed in a bone and showing an exploded view in perspective of a cap that fits over the top of the implant which is an optional feature of this invention.

FIG. 13 is an exploded view in perspective and showing in perspective a fragmentary implant inserted into a void and exemplifies an option that can be used with any of the embodiments described herein or any other embodiments falling within the scope of this invention. The cover or cap generally illustrated by reference numeral 70 is designed to fit over the upper end of the L-shaped members and is shaped such that the ends are outwardly bent to conform to the shape of the top portion of the implant. Internal parallel shaped extending members 72 and 74 fit internally in the implant and serve to enhance the rigidity of the cap. Obviously, the shape of the implant and cap configuration can take many forms without departing from the scope of this invention. The cover or cap serves to retain biologically compatible material that typically fills the void as was described in the above paragraph.

Figure 14:
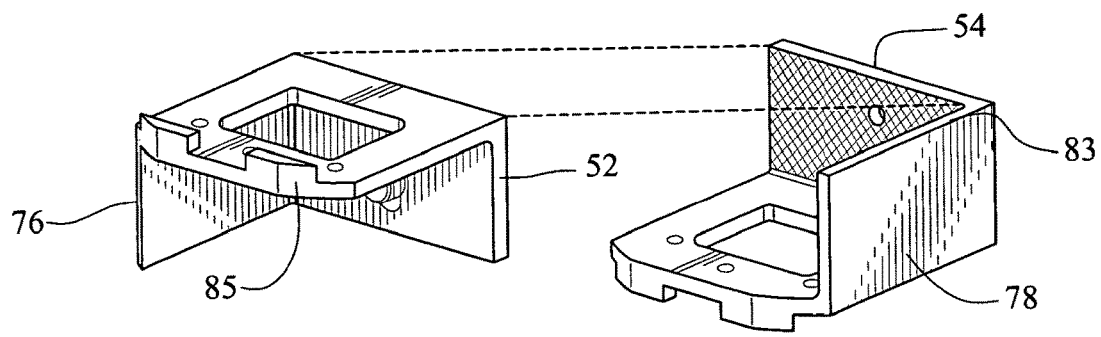
FIG. 14 is an exploded view in perspective of another embodiment of this invention.

FIG. 14 is an exploded view in perspective and is similar to the embodiment depicted in FIG. 12 exemplifying another embodiment where the sides of the implant are closed in by virtue of the wall portions 76 and 78 extending from the upstanding arm of the L-shaped member. Obviously, the embodiment depicted in FIG. 14 is substantially the same as the embodiment depicted in FIG. 7 save for the right angle extending portions 76 and 78. This implant may also include the laterally extending projections 85, that function similarly to the lateral projections 48 of FIG. 2A.

Figure 15:
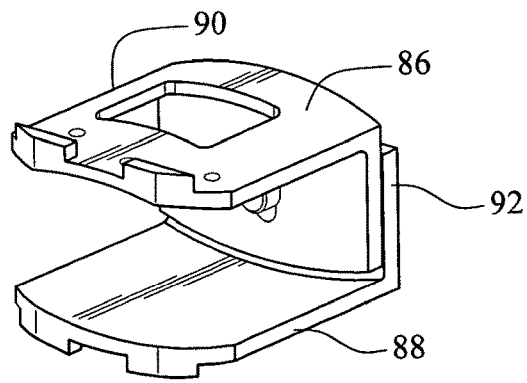
FIG. 15 is a view in perspective on another embodiment of this invention.

The embodiment illustrated in FIG. 15 is substantially the same as the embodiment depicted in FIG. 8 except that the upstanding arms 86 and 88 of the L-shaped members 90 and 92, respectively are configured in a concave shape.

Figure 16:
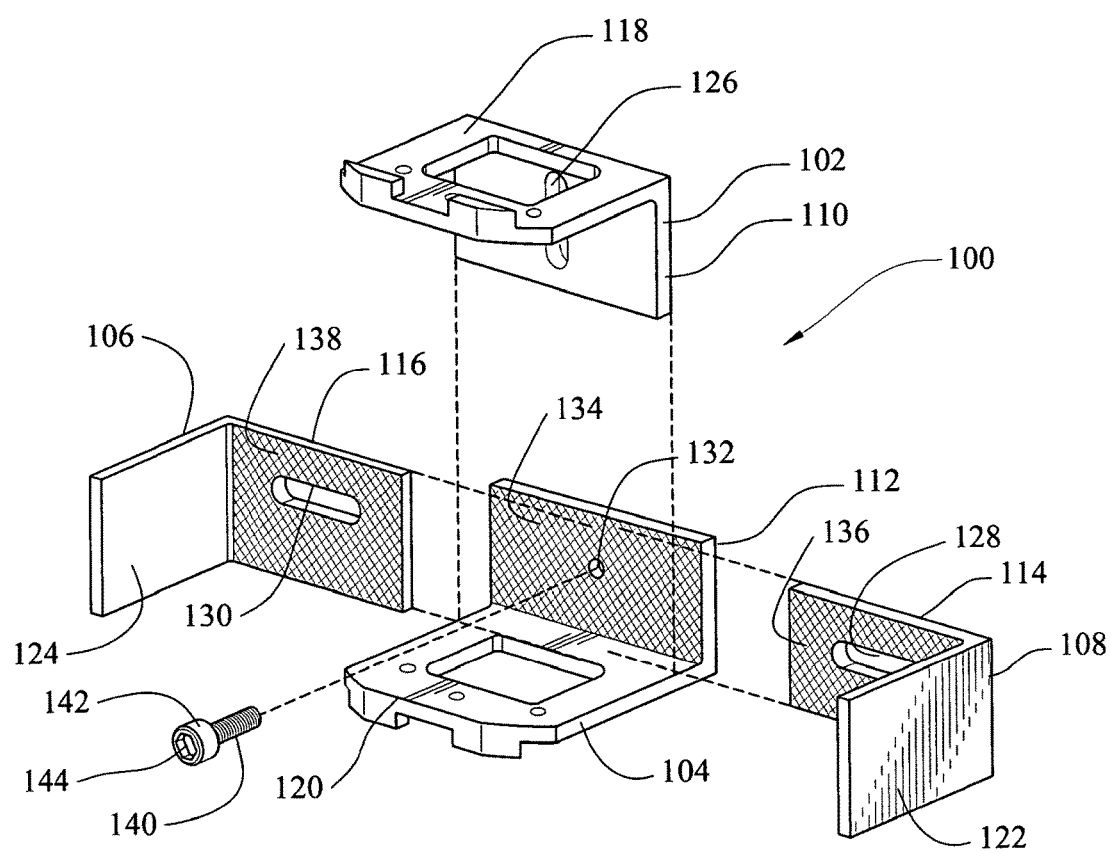
FIG. 16 is an exploded view in perspective illustrating another embodiment of this invention.

The embodiment of FIG. 16 exemplifies another version of the implant generally illustrated by reference numeral 100 that essentially includes four sides 102, 104, 106 and 108 all of which are L-shaped in design including a base arm 110, 112, 114 and 116, respectively and an upstanding arm 118, 120, 122 and 124 respectively. Each of the base arms 110, 114 and 116 include slots 126, 128 and 130, respectively and the base arm 112 includes a threaded hole 132. Preferably, the mating surface of the sides 104, 106 and 108 include the roughened surfaces 134, 136 and 138, respectively for better holding. Similar to the other embodiments, this embodiment includes a threaded screw 140 with the head 142 and tool receiving recess 144. Obviously, the base arms of the four walls are placed in an overlapping position and the screw is threaded. It is apparent from the foregoing that when this embodiment is assembled the walls are not only expandable but they can be moved angularly.

What has been shown by this invention is an implant that is capable of filling the void in regular or irregular shaped voids formed in a vertebra or bone or is capable of being placed adjacent to vertebrae or bones with various configurations. As is disclosed above, the implant can be oriented so that the superior aspect of the implant will engage the inside surface of the superior aspect of the vertebral body, endplate, or surface and the inferior aspect of the implant will engage the inside surface of the inferior aspect of the vertebral body, endplate, or surface. The inventive implant itself may be constructed of many different materials to fit the needs of the patient and surgeon. The inventive nature of the implant design makes it compatible with many different materials in which it may be manufactured including as examples; titanium, stainless steel, ceramic, peek, and bio-resorbable and/or radiolucent materials just to name a few. Additionally, the description of this application illustrates various species of this invention and while the particular implant may be individually sold, it is preferred that a series of implants of different sizes and/or of different characteristics be sold as a kit so that the surgeon has at his disposal the immediate selection of the particular implant suitable to a particular size and shape of the void created in the operation.

Although this invention has been shown and described with respect to detailed embodiments thereof, it will be appreciated and understood by those skilled in the art that various changes in form and detail thereof may be made without departing from the spirit and scope of the disclosed invention.

We claim:

1. A method of placing an implant into an iatrogenically created skeletal void within an individual vertebral body, the method comprising:
   creating a void by removing at least a portion of the individual vertebral body while leaving superior and inferior endplates functionally intact, the void extending through the individual vertebral body from an anterior wall through a posterior wall; and
   placing the implant within the void between the superior endplate and the inferior endplate of the individual vertebra such that the implant does not engage with adjacent vertebra thereby permitting the endplates to perform their function.

2. The method of claim 1, wherein placing the implant further comprises adjusting the implant to fit within the void.

3. The method of claim 2, wherein adjusting the implant to fit the void comprises expanding the implant to contact innermost surfaces of the individual vertebral body.

4. The method of claim 1, wherein the implant is configured to supplement the individual vertebral body and serve as an artificial vertebral body without eliminating movement of the individual vertebral body.

5. The method of claim 1, wherein placement of the implant repairs the void in the individual vertebral body.

6. The method of claim 1, further comprising filling the implant with biocompatible material.

7. The method of claim 1, wherein the implant, after placement in the void, engages at least one of the superior endplate and the inferior endplate.

8. The method of claim 1, wherein creating the void includes dissecting bone across the individual vertebral body in a direction from the anterior wall towards the posterior wall, leaving the inferior endplate and the superior endplate sufficiently intact after the dissection.

9. The method of claim 1, wherein placing the implant within the void supports at least one of the superior endplate and the inferior endplate.

10. The method of claim 1, the implant including a frame, wherein after insertion within the void, the frame of the implant is used to support the superior and inferior endplates.

11. The method of claim 1, wherein creating the void by removing at least a portion of the individual vertebral body allows access to an opposite side of the individual vertebral body.

12. A method of placing an implant into an iatrogenically created skeletal void within an individual vertebral body, the individual vertebral body having a superior endplate and an inferior endplate, the method comprising:
   creating a void by removing bone from at least a portion of the individual vertebral body from a primarily anterior position toward a primarily posterior direction while leaving superior and inferior endplates functionally intact, the void extending through the individual vertebral body from an anterior wall through a posterior wall; and
   placing the implant within the void between the superior endplate and the inferior endplate of the individual vertebral body such that the implant does not engage with adjacent vertebra thereby permitting the endplates to perform their function.

13. The method of claim 12, wherein placing the implant further comprises adjusting the implant to fit within the void.

14. The method of claim 13, wherein adjusting the implant to fit the void comprises expanding the implant to contact innermost surfaces of the individual vertebral body.

15. The method of claim 12, wherein the implant is configured to supplement the individual vertebral body and serve as an artificial vertebral body without eliminating movement of the individual vertebral body.

16. The method of claim 12, wherein placement of the implant repairs the void in the individual vertebral body.

17. The method of claim 12, further comprising filling the implant with biocompatible material.

18. The method of claim 12, wherein the implant, after placement in the void, engages at least one of the superior endplate and the inferior endplate.

19. The method of claim 12, wherein creating the void includes dissecting bone across the individual vertebral body leaving the inferior endplate and the superior endplate sufficiently intact after the dissection.

20. The method of claim 12, wherein placing the implant within the void supports at least one of the superior endplate and the inferior endplate.

21. The method of claim 12, wherein creating the void by removing bone from at least a portion of the individual vertebral body allows access to an opposite side of the individual vertebral body.

22. A method of placing an implant within an iatrogenically created skeletal void within an individual vertebral body, the individual vertebral body having a superior endplate and an inferior endplate, the method comprising:

removing bone between the superior endplate and the inferior endplate of the individual vertebral body, the removal of the bone creating a void extending through the individual vertebral body from an anterior wall through a posterior wall leaving the superior and inferior endplates functionally intact; and placing the implant within the void thereby permitting the endplates to perform their function.

23. The method of claim 22, wherein placing the implant further comprises adjusting the implant to fit within the void.

24. The method of claim 23, wherein adjusting the implant to fit the void comprises expanding the implant to contact innermost surfaces of the individual vertebral body.

25. The method of claim 22, wherein the implant is configured to supplement the individual vertebral body and serve as an artificial vertebral body without eliminating movement of the individual vertebral body.

26. The method of claim 22, wherein placement of the implant repairs the void in the individual vertebral body.

27. The method of claim 22, further comprising filling the implant with biocompatible material.

28. The method of claim 22, wherein the implant, after placement in the void, engages at least one of the superior endplate and the inferior endplate.

29. The method of claim 22, wherein placing the implant within the void supports at least one of the superior endplate and the inferior endplate.

30. The method of claim 22, wherein creating the void allows access to an opposite side of the individual vertebral body.

* * * * *